United States Patent [19]

Marple et al.

[11] Patent Number: 4,670,135

[45] Date of Patent: Jun. 2, 1987

[54] HIGH VOLUME VIRTUAL IMPACTOR

[75] Inventors: Virgil A. Marple, Maple Plain; Benjamin Y. H. Liu, North Oaks, both of Minn.

[73] Assignee: Regents of the University of Minnesota, Minneapolis, Minn.

[21] Appl. No.: 879,471

[22] Filed: Jun. 27, 1986

[51] Int. Cl.[4] .............................................. B07B 7/086
[52] U.S. Cl. ...................... 509/143; 55/270; 55/431; 55/482; 73/28; 73/865.5; 209/145
[58] Field of Search ............... 209/133, 142, 143, 145; 73/28, 865.5; 55/270, 482, 431

[56] References Cited

U.S. PATENT DOCUMENTS

| | | | |
|---|---|---|---|
| 3,901,798 | 8/1975 | Peterson | 209/143 |
| 4,132,894 | 7/1979 | Yule | 73/28 |
| 4,133,202 | 1/1979 | Marple | 73/28 |
| 4,301,002 | 11/1981 | Loo | 209/143 |
| 4,321,822 | 3/1982 | Marple et al. | 73/28 |
| 4,358,302 | 11/1982 | Dahneke | 55/270 |
| 4,452,068 | 6/1984 | Loo | 73/28 |
| 4,545,897 | 10/1985 | Masuda | 209/143 |

FOREIGN PATENT DOCUMENTS 1273266 5/1972 United Kingdom ............... 209/143

OTHER PUBLICATIONS

Marple, Virgil A. and Chung M. Chien, "Virtual Impactors: A Theoretical Study," *Environmental Science and Technology*, 14:976, pp. 976–985, 1980.

Novick, V. J., J. L. Alvarez and A. D. Appelhans, "Design of a Multi-Stage Virtual Impactor," *Aerosols*, Elsevier Science Publishing Co., Inc., pp. 143–145, 1984.

Solomon, Paul A., Jarvis L. Moyers and Robert A. Fletcher, "High-Volume Dichotomous Virtual Impactor for the Fractionation and Collection of Particles According to Aerodynamic Size," *Aerosol Science and Technology*, vol. 2, pp. 455–464, 1983.

*Primary Examiner*—Randolph A. Reese
*Assistant Examiner*—Donald T. Hajec
*Attorney, Agent, or Firm*—Kinney & Lange

[57] ABSTRACT

A high volume virtual impactor for sampling atmospheric aerosols has a plurality of inlet nozzles and associated receiving tubes mounted in a common frame or housing having passageways which divide the airflow through the inlet nozzles into a major flow and a minor flow. The minor flow, or the smaller volume flow, passes through the respective receiving tube into a common chamber, while the major flow is caused to turn 180° between flow exit of the inlet nozzle and its associated receiving tubes and pass as through a small particle filter. The impactors are arranged in oppositely facing and aligned pairs. The exhaust ends of the receiving tubes in a part face each other, so that the flows from the receiving tubes will intermix in the center of a chamber, to prevent substantial particle impingement against the housing surfaces. The filters are located at the bottom of the housing to minimize losses. Use of several parallel vertical impactor inlet nozzles and receiving tubes permits a high total flow rate while keeping the flow rate through any individual tube at a reasonable value and thus within good operating parameters. Because the input nozzles and receiving tubes are mounted in a single frame, the mounting holes for them can be machined precisely to insure near perfect alignment and thus enhance operation.

12 Claims, 3 Drawing Figures

HIGH VOLUME VIRTUAL IMPACTOR

ACKNOWLEDGEMENT

The inventors gratefully acknowledge support from the United States Environmental Protection Agency. The United States Government has certain rights in the invention described and claimed in this application.

BACKGROUND OF THE INVENTION

1. Field of the Invention.

The present invention relates to high volume virtual impactors for collection of samples of particles carried in the air.

2. Description of the Prior Art.

Virtual impactors have been known in the prior art. Virtual impactors include an input nozzle aligned with a receiving tube. Air carrying particles to be collected is drawn through the input nozzle and separated into major flow and minor flow. The major flow is diverted from entering the receiving tube while the minor flow passes into the receiving tube along with the large particles, which are carried into the receiver tube in inertia. The air is then filtered for analysis of the particles.

U.S. Pat. No. 4,301,002 illustrates such a device, and shows a single virtual impactor apparatus mounted in a frame for handling relatively low volume flows. The receiving tube in Patent '002 has its end closed with a large particle filter, while the major flow is diverted from the receiving tube and passes through a separate small particle filter. A single air pump or blower is used for providing the separated major and minor flows needed.

The virtual impactor shown in U.S. Pat. No. 4,301,002 shows some of the problems associated with this type of collector, as well as indicating advantages, but it provides no solution to the problem of handling relatively large flows and obtaining reliable samples.

U.S. Pat. No. 4,452,068 also shows a device for trapping aerosols, utilizing flow separation principles, but having a grooved impaction surface for receiving the inlet air and providing an inertial trap for particles coming from the inlet.

Impactor devices for collecting airborne particles are shown in U.S. Pat. Nos. 4,133,202, issued to Marple on Jan. 9, 1979, and 4,321,822, issued to Marple et al. on May 30, 1982.

In the article entitled "Virtual Impactors: A Theoretical Study", (by Marple et al., Environmental Science & Technology, 1980, 14, 976), the characteristics of virtual impactors are analyzed as to operation, effect on collection using different dimensions of nozzles, and other constructional factors. Also, in Aerosol Science and Technology 2:455–464 (1983) Solomon et al. published a study on a High-Volume Dichotomous Virtual Impactor for the Fractionation and Collection of Particles According to Aerodynamic Size. This study used a single acceleration nozzle for the virtual impactor.

A multi-stage virtual impactor, which used a single flow but had more than one stage of separation is disclosed and discussed in a paper entitled Design of a Multi-Stage Virtual Impactor by Novick et al. and published in the work *Aerosols*, Liu, Pui, and Fissan, editors, Elsevier Science Publishing Co., Inc. (1984).

Up to now, however, high volume virtual impactors that preserve the integrity of the samples collected, avoid excessive impaction of the particles on housing surfaces, and permit collection of aerosol samples quickly for practical application in the field have not been advanced. The present device provides such an impactor.

SUMMARY OF THE INVENTION

A high volume virtual impactor apparatus has a plurality of virtual impactors each having an inlet nozzle and a receiving tube arranged on a housing or frame for parallel flow and which are utilized to obtain a high flow rate while keeping the flow rate through each individual virtual impactor at a reasonable value, and thus at good operating conditions. The housing has walls in which the inlet nozzles or tubes for the impactors are mounted, and parallel walls for mounting the respective associated receiving tube. The mounting openings and holes for the inlet nozzles and the receiving tubes can be machined at the same time for precise alignment.

The virtual impactor receiving tubes open into a common chamber, and are arranged in opposed pairs so that the exhaust opening of each receiving tube faces the exhaust or outlet of another receiving tube and thus the flow exiting from one receiving tube will be directed toward the flow coming from the other tube of the opposed pair. The exhaust flows intermix and stagnate to permit the particles carried by such flows to be dropped onto a filter prior to striking any surfaces or being lost or damaged. The flows from the receiving tube are filtered in a large particle filter.

The inlet nozzles and receiving tubes of each inertial impactor are separated and a major portion of the flow through each nozzle is diverted from its receiving tube, and this major flow carries the smaller particles that do not have sufficient inertia to be carried into the receiving tubes. A small particle filter also is provided as shown. The small particle filter is mounted in a filter cassette also holding the large particle filter, so that all particles carried in the flow are collected. The filter cassette permits mounting the filters in a laboratory and quickly placing them into position on the housing when a sample is to be taken, and then taking the entire filter cassette back to the laboratory for removal of the filters and for analysis. This insures that the sample collected will be handled properly to avoid losses and insure the integrity of the sample.

The entire assembly of the housing and filter cassette is compact, with the housing being of such size that it can be easily mounted in existing separator housings.

The virutal impactor can be controlled to give precise size classification of the particles being collected.

DETAILED DESCRIPTION OF THE PREFERRED EMBODIMENT

Figure 1:
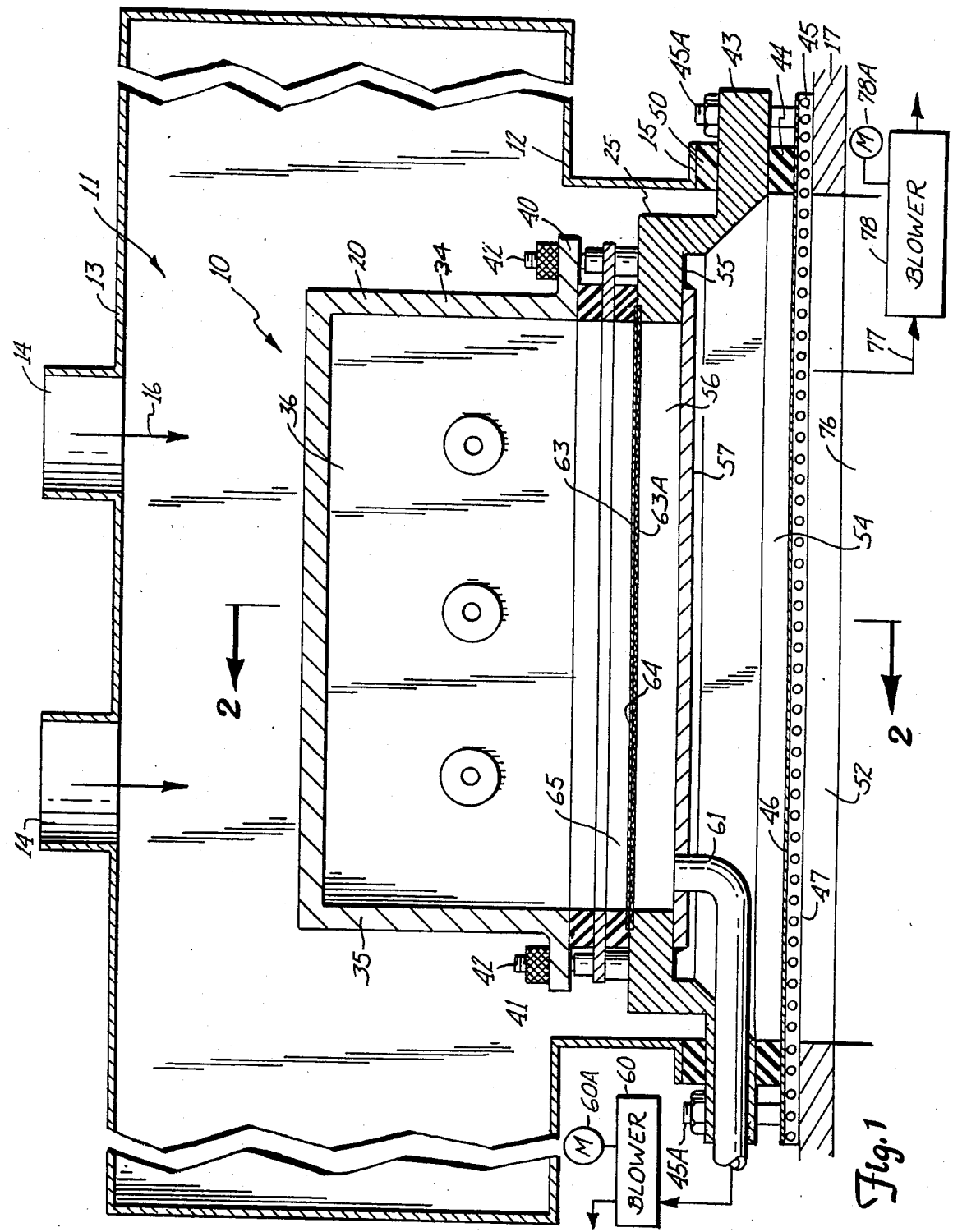
FIG. 1 is a fragmentary view of a plenum chamber mounting a high volume virtual impactor made according to the present invention, which is shown in cross section.

As shown in FIG. 1, a high volume virtual impactor 10, made according to the present invention, is mounted in a conventional plenum chamber 11 of a particle classifier of conventional design. The chamber 11 is defined by a lower wall 12 and an upper wall 13 that has a plurality of inlet openings 14. The plenum chamber walls are hinged to the lower portion of the classifier, including a divider wall 17 so that the plenum chamber walls can be lifted up to provide access to the virtual impactor 10. The walls include a flange 15 which can be gasketed to surround the virtual impactor housing. The virtual impactor housing is mounted in an opening forming an exhaust opening from the plenum chamber.

The only exit from the plenum chamber 11 is through the virtual impactor apparatus 10. The air is made to flow generally as indicated by the arrows 16, through the openings 14 to the virtual impactor apparatus 10. The plenum chamber is of sufficient size for the desired operation. Preferably the air entering the plenum chamber 11 through the openings 14 will be preclassified so only particles under 10 microns effective aerodynamic diameter are present.

As shown, the virtual impactor apparatus includes a housing or frame 20 that supports the virtual impactor tubes and assemblies, and which is adapted to be mounted onto a base filter cassette 25, which in turn is mounted onto the divider wall 17 of the classifier mounting the plenum chamber 11. As can perhaps best be seen in FIGS. 2 and 3, the housing 20 has outer side walls 30 and 31, respectively, and partition walls 32 and 33, respectively. The walls 30–33 are parallel. In addition, the housing 20 has walls 34 and 35 which extend laterally to walls 30 and 31 and together with walls 32 and 33 form chambers including a center chamber 36, and outer side chambers 37 and 38, respectively. Chambers 36, 37 and 38 are open at the bottoms thereof. As can be seen, the end walls 34 and 35 have mounting flanges 40 and 41 thereon. The mounting flanges have provided openings for receiving bolts 42 that in turn are coupled to the base filter cassette 25 and hold the base filter cassette 25 in position on the housing 20.

As can be seen, the base filter cassette 25 includes a main mounting flange 43 that surrounds the periphery of the base filter cassette. A small particle filter assembly 45 is mounted on the cassette and has a screen frame with bolts 45A extending therefrom. The small particle filter attaches with the bolts 45A to the lower side of the flange 43. A gasket 44 is positioned between the small particle filter assembly 45 and the lower surface of flange 43. The small particle filter assembly 45 includes a support screen 47, which supports and retains a paper filter 46 on the top surface of the screen when the screen is clamped in place on flange 43. Other suitable support members can be used if desired.

The bolts 45A are fixed to the frame for screen 47 and pass through provided openings in the flange 43 to permit securing the screen 47 in place on the cassette 25 through the flange 43.

As shown, a flange 15 on wall 12 overlies the flange 43, and a gasket 50 is used for sealing the flange 15 relative to the flange 43 when the walls from the plenum chamber are held closed. The flange 15 surrounds the housing 20 to seal on cassette flange 43. This means that the opening indicated at 52 defined through the wall 17, and through which the major flow from the virtual impactor will pass, is sealed from the exterior, and is open to the plenum chamber 11 only through the opening indicated at 54 defined by the flange 43.

Figure 2:
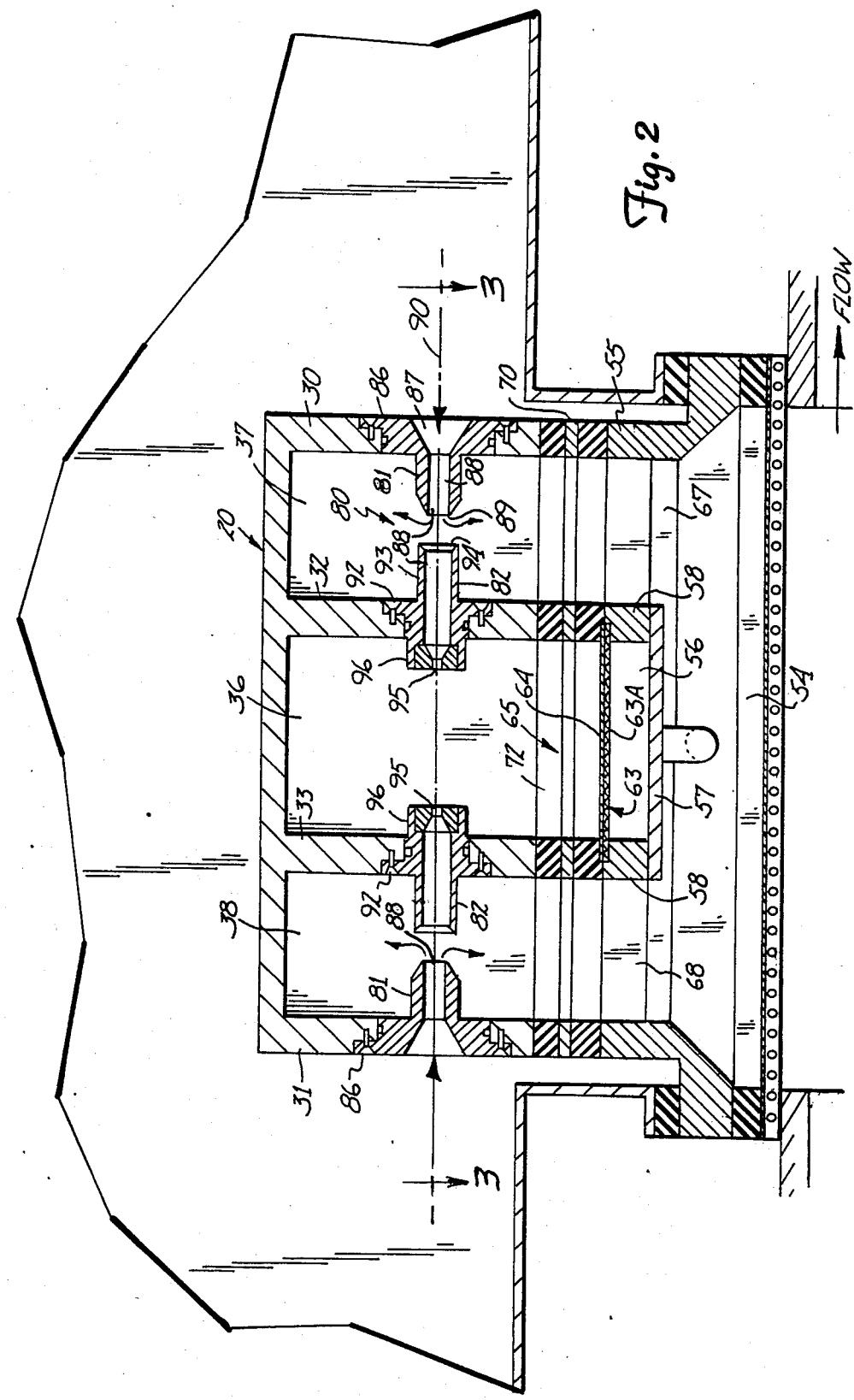
FIG. 2 is a sectional view taken generally along line 2—2 in FIG. 1.

As can be seen, the flange 43 extends inwardly and has a rim 55 on its support side that fits within the periphery of flange 15 on the wall 12 of the plenum chamber. A separate chamber 56 is defined within the perimeter of rim 55. The end walls of the chamber 56 are formed by rim 55, and the side walls are formed by cross pieces 58 (see FIG. 2) which are directly under and aligned with walls 32 and 33. The bottom of chamber 56 is closed with a plate 57. Chamber 56 is the large particle chamber and as shown in FIG. 2 is positioned below the chamber 36 in the center of the housing 20 and is open to the chamber 36.

Chamber 56 (and thus chamber 36) is connected to a suitable blower 60 through a tube 61. The blower 60 comprises an air pump that draws an airflow through the chamber 56 and thus from the chamber 36 through a large particle filter assembly indicated schematically at 63. The large particle filter 63 has a support screen 63A, and includes a paper filter 64 supported on the top surface of the screen 63A.

A gasket 65 overlies the rim 55 and has cross members that overlie cross members 58. The gasket 65 thus overlies the edges of the filter assembly 63 to hold the filter assembly in place. As can be seen the gasket 65 provides an opening that leads from the central chamber 36 to the chamber 56. The gasket 65 also defines openings that are in registry with side openings 67 and 68, leading to the opening 54 of the filter cassette flange 43 from the respective chambers 37 and 38 in the housing 20.

A clamp plate 70 is formed to the shape of the gasket 65 with a peripheral rim and cross member in registry with cross members 58. A second gasket 72 that is identical to gasket 65 overlies clamp plate 70, so that there are through passageways to each of the chambers 36, 37 and 38 in the housing 20, leading to the respective filter assemblies, but the gaskets insure that there is a fluid seal separating chambers 36 and 56 from chamber 36 and 37. The gaskets prevent air leaks at the interfaces between the housing 20 and the filter cassette.

The opening 54 in the filter cassette 25 aligns with the opening 52 in wall 17 which leads to a chamber indicated schematically at 76 that is connected through a suitable conduit indicated schematically by the line 77 to a second blower or air pump 78. The blower 78 forms an air pump for providing the major portion of the flow through the virtual impactor assembly 10.

The housing 20 and filter cassette 25 are made so that the only air inlets to the blowers 60 and 78 are through the virtual impactor housing 20.

As shown, the housing or frame 20 supports six virtual impactor assemblies 80 arranged for parallel flow. The virtual impactor assemblies 80 each include an inlet nozzle or tube 81 and an aligning receiver tube or receptor 82. The inlet nozzles or tubes 81 are mounted in the side walls 30 and 31, respectively, and as shown have the nozzle mounting flanges 83, and have a generally conical inlet passageway portion 87 that tapers down (constricts) to a nozzle passageway 88 which defines an outlet providing a jet directed toward an aligning receiver tube 81. The nozzle passageway 88 and conical inlet passageway 87 have a central axis 90.

The receiver tubes or receptors 82 for each of the virtual impactor assemblies 80 are mounted on the walls 32 and 33, respectively, and each receiver tube 82 includes a mounting flange 92, and a tube portion 93 having an inlet opening 94 that is spaced from the outlet or exhaust end of the nozzle opening 88, as can be seen. The inlet end 94 of the receiver tubes has a tapered edge as shown for guiding the flow smoothly into the interior passageway of the receiver tube. The exhaust end or outlet of each receiving tube has an orifice member 96 defining a restricted orifice exhaust opening 95 that provides a pressure drop for controlling the flow, so that there is identical flows through each of the receiver tubes. Each of the inlet nozzles or tubes 81 also reduces to form a restriction so flow is equalized between the nozzles.

Figure 3:
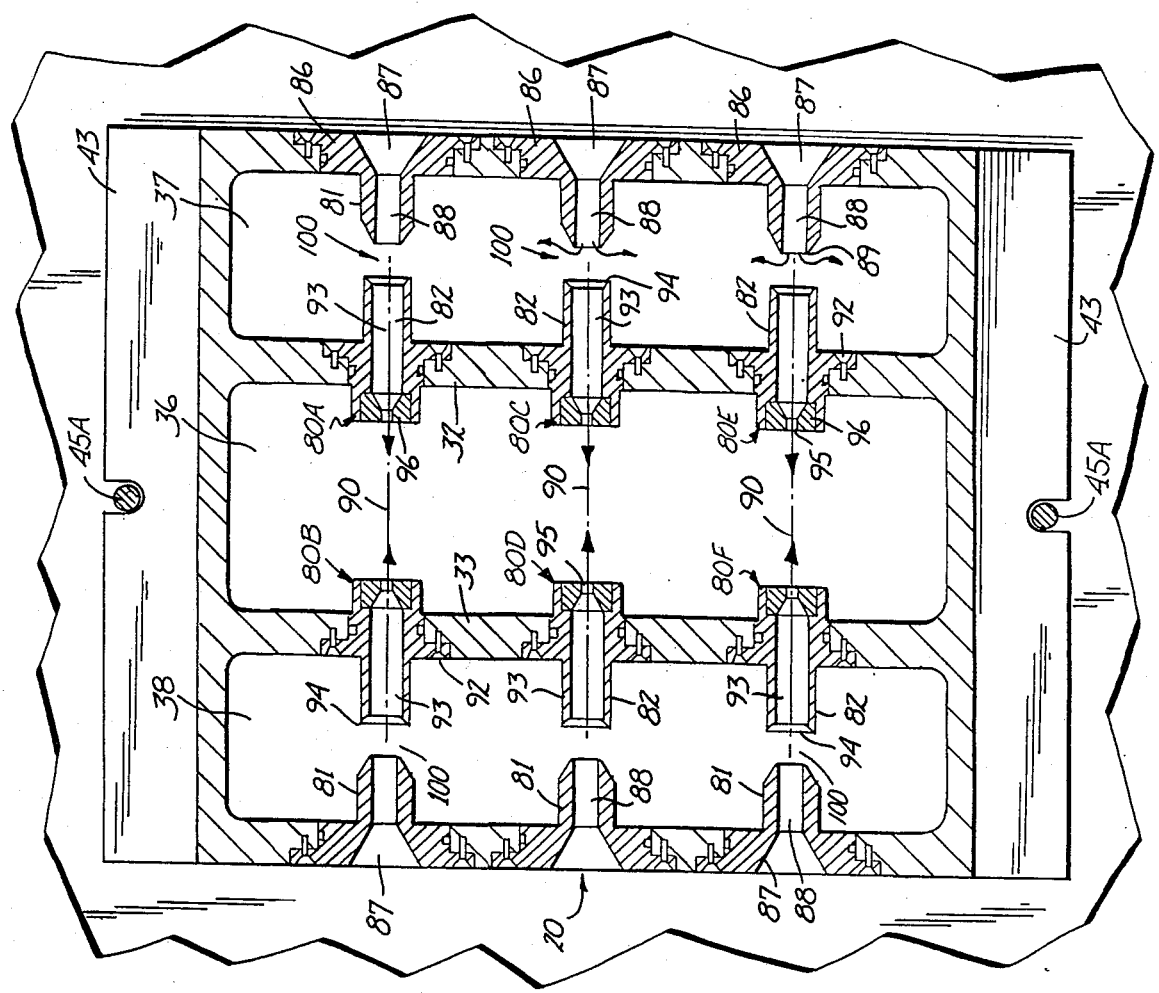
FIG. 3 is a sectional view taken generally along line 3—3 in FIG. 2.

The exhaust or outlet openings 95 of each of the receiver tubes 82 opens into the chamber 36. Thus, all of the receiver tubes exhaust into the chamber 36. As can be seen in FIGS. 2 and 3, the virtual impactors 80 are arranged so that the exhaust outlet openings of each receiver tube is directly opposite and aligned along the axis 90 (which also is the axis of the receiver tubes) with the exhaust opening of a receiver tube of an opposed virtual impactor. In other words, there is a first pair of virtual impactors 80A and 80B, the individual units of which are directly opposed and coaxial, a second pair of virtual impactors 80C and 80D, again having the axes of the receiver tubes, and of the orifice defining the exhaust openings 95 coaxial, and a third pair of virtual impactor assemblies 80E and 80F. The receiver tubes 80E and 80F also has the exhaust openings of the receiver tubes coaxial and directly opposed across the width of the chamber 36 as can be seen in FIG. 3.

As shown, the outlet opening 89 of each of the nozzle passageways 88 of the nozzles 81 is spaced as shown at 100 from the inlet opening 94 of its respective receiver tube. This space 100 provides a flow path into the respective chambers 37 and 38, and thus flow that is created by blower 78 will be drawn through openings 100, through the openings 67 and 68 and into the opening 54 of the filter cassette frame or flange 43 and then through the opening 52 into a chamber provided and then to the blower 78 powered by a motor 78A.

An air flow is established by blower 60 (powered by a motor 60A) out of the receiver tubes, into chamber 36 and through the openings in the gaskets and plate 70 to the chamber 56 and then through the filter assembly 63 including the paper filter 64. The chamber 56 is separated or sealed from opening 54 and thus the flow from chamber 36 is separate from the flows from chambers 37 and 38.

As has been shown in the prior art, the flow exiting through the blower 78 drawn through the small particle filter is called the major flow, and the flow through the spaces 100 in chambers 37 and 38 is substantially larger than that through the receiver tubes 82 and out the exhaust orifice openings 95. Essentially, the flow through the receiver tubes 82 and out the exhaust openings 95 is approximately five percent of the flow through the space or openings 100 and through the small particle filter. Thus, for example, if the virtual impactor device is designed for a flow of 40 cubic feet per minute, there will be 38 cubic feet a minute through the blower 70, and two cubic feet per minute through the blower 60.

Large particles of pollen, dirt, and other aerosols carried by the ambient air that comes in through the inlet openings 14 into the plenum chamber 11 are carried through the inlet openings 87 of the nozzles or inlet tubes 81, and the flow through the nozzle passageways 88 is axially aligned with an directed toward the associated receiver tube. The major flow, however, is diverted out through the spaces or openings 100 and through chambers 37 and 38. The major flow does not enter the receiver tubes. The larger particles, however, have sufficient inertia so that they are carried into the respective receiver tubes, and then the minor flow, supplied by the blower 60, will be sufficient to carry these particles through the exhaust orifice openings 95 into the chamber 36.

Because the flows through each of the openings 95 of each associated pair of receiver tubes are directly facing or opposed with the exhaust opening of the other receiver tube of the pair of virtual impactors, the minor flows interface or collide in the center portions of the chamber 36, slowing the flow and dropping the large particles downwardly onto the filter assembly 63 without striking surfaces of the walls defining chamber 36. The minor flow coming out through the tube 61 from chamber 56 will insure that the paper filter 64 will separate out the large particles that are carried into the chamber 36.

The total major flow passes out through both chambers 37 and 38, and through openings 67 and 68 and through the small particle filter assembly 45. The paper filter 46 of filter assembly 45 collects the small particles as the major flow is exhausted through the blower or pump 78. The major flow carrying the small particles is classified as to particle size by the fact that the flow has to turn substantially 90° between the nozzles 88 and the associated receiver tube 82. The inertial separation provides a sharp classification of particle sizes, because the large particles have enough inertia to penetrate into the receiver tube and pass out the receiver tube with the minor flow through the exhaust openings 95. The smaller particles, having less inertia, will not penetrate into the receiving tubes as deeply and will be carried with the major flow even though they may enter into the inlet end of the receiving tube a short distance before being carried with the major flow.

The virtual impactors have been found to work well where the division size between large particles and small particles is in the range of 2.5 microns equivalent aerodynamic diameter of the particles. Usually the virtual impactor assembly 10 will be used after an initial separation step so that the particles in the plenum chamber 11 will be smaller than 10 microns for example, and thus the large particles passing through the receiver tubes 82 into the chamber 36 will be between 2.5 and 10 microns in size, and the particles passing with the major flow will be under 2.5 microns in equivalent aerodynamic diameter.

The orifices 96 forming the exhaust openings 95 are selected in size so that they will provide for flow control to equalize the flows through each of the receiver tubes of the virtual impactor assemblies 80.

It is essential that the flows in the chambers 37 and 38 and the chamber 36 be controlled, and while this is done with two blowers in the present disclosed device, it can be done with flow control orifices using a single blower if desired. Because the flow through each of the six nozzles is equal, the nozzle diameters and the pressure drops across the nozzles are also identical.

By using a plurality of parallel flow virtual impactor stages a high flow rate can be obtained while the flow through any of the virtual impactors is held at a reasonable value, and because the virtual impactor receiver tubes are arranged in opposed pairs with the receiver tube outlets aimed directly at each other, the jets through the exhaust openings stop flow from the other jet of its pair and cause the particles to drop out without impacting against any wall surface.

The filters for both the large and small particles are on the floor of the chambers and thus below the virtual impactors, so that the particles will drop down onto the filters to minimize large particle losses from the point where they are separated or classified to where they are collected on the filter.

The unit is compact and will go onto existing equipment for high volume samplers easily.

As shown, the filter cassette 25 is a separate assembly that carries both the large particle filter and the small particle filter, so that the filters can be loaded in a laboratory, transported to the field, and the housing 20 can be attached using bolts 42. The housing filter assembly is placed into the plenum chamber 11 for a specified sampling period during which the blowers are operated. The filter cassette can then be removed and returned to the laboratory for changing the filters quite easily.

Also, it can be seen in FIG. 2 in particular that the flanges 86 and 92 of each of the virtual impactor inlet tubes and receiver tubes are coaxial and mounted onto closely spaced parallel walls on a common frame, so that the mounting openings can be machined at the same time so that the inlet tubes or nozzles and the receiving tubes can be in near perfect alignment and perfectly coaxially. The flange 86 and mounting opening for the flanges in walls 30 and 31 are larger than the flange 92 and its mounting opening to aid in machining the openings in walls 32 and 33. Close alignment of the nozzles and the associated receiver tube is necessary for correct operation of a virtual impactor.

Thus the unit is easily made, highly efficient, and provides for high flow rates utilizing virtual impactors.

What is claimed is:

1. A high volume virtual impactor for collection of particles suspended in air according to aerodynamic size comprising:
   means providing an inlet for a fluid carrying particles to be collected;
   a frame;
   a plurality of inlet nozzle means and a plurality of receiver tubes having inlet ends for receiving airflow from said nozzle means supported on the frame, said receiver tubes having exhaust ends, and the receiver tubes being supported in opposed pairs with the exhaust end of each receiver tube facing the other receiver tube of its respective pair;
   said nozzle means and the inlet ends of said receiver tubes being spaced apart, and fluidly isolated from the exhaust ends of the receiver tubes;
   means for providing a first predetermined volume of flow of air out through the space between the nozzle means and the inlet ends of the respective receiver tubes;
   means for providing a second predetermined volume of flow of air between the exhaust ends of the opposed pairs of receiver tubes; and
   first and second filter means mounted on the frame for separately filtering the first and second predetermined volumes of air, the first predetermined volume of air being substantially greater than the second predetermined volume of air.

2. The apparatus as specified in claim 1 wherein said opposed pairs of receiver tubes have restrictor orifices to ensure substantially equal volumes of fluid flowing through the receiver tubes.

3. The apparatus as specified in claim 2 wherein said nozzle means form restrictions from their inlets to their outlets, the outlets of said nozzle means being adjacent the inlet ends of the receiver tubes.

4. The apparatus as specified in claim 3 and means forming a plenum chamber containing air forming the first and second predetermined volume of flow.

5. The apparatus as specified in claim 2 wherein said frame comprises a housing having wall means defining first and second chambers adjacent opposite sides thereof and a separate central chamber between the first and second chambers, the inlet ends of each receiver tube of the respective opposed pair of receiver tubes being in the first and second chambers respectively, and the exhaust end of both receiver tubes in each associated pair of receiver tubes opening to the central chamber.

6. The apparatus of claim 5 wherein the means to provide the second predetermined volume of flow of air is coupled to the central chamber.

7. The apparatus of claim 5 wherein the first filter means is positioned below the exhaust ends of the receiver tubes.

8. A high volume virtual impactor for collection of particles classifed according to aerodynamic size comprising:
   means providing a fluid carrying particles to be classified;
   a housing having first and second end walls and third and fourth partition walls spaced from the end walls and on the interior of said housing;
   a plurality of inlet nozzle means mounted in each of the end walls, a plurality of receiver tubes mounted on each partition wall, each receiver tube being positioned coaxial with one nozzle means for receiving airflow from said one nozzle means, said receiver tubes having inlet ends facing the respective nozzle means and exhaust ends, the receiver tubes being supported in opposed pairs with the exhaust end of each receiver tube facing the other receiver tube of its respective pair across a central chamber defined by the partition walls;
   the end walls and the respective adjacent partition wall forming end chambers separated from the central chamber, said nozzle means and the inlet ends of the respective receiver tubes being spaced apart, with the space being in one of said end chambers;
   means for providing a flow of a first predetermined volume of air from said central chamber;
   means for providing a flow of a second substantially greater predetermined volume of air from said end chambers;
   filter means for separately filtering the air passing from the central chamber and from the end chambers; and
   the spacing of the exhaust ends of the receiver tubes of each opposed pair being such that the airflow from the exhaust ends of each pair intermix in the central chamber.

9. The apparatus of claim 8 wherein said filter means comprise a large particle filter for filtering air from the central chamber and a small particle filter for filtering air from end chambers;
   a filter cassette frame mounting both of said filters, wall means on said cassette frame to form a separate chamber isolating the large particle filter from the small particle filter carried thereby, the means for providing a flow of the first predetermined volume of air being coupled to the separate chamber to draw the first predetermined volume of air through the large particle filter; and means to removably mount the housing on the filter cassette frame with the central chamber open to the separate chamber through the large particle filter.

10. The apparatus of claim 9 wherein the filter cassette frame supports the small particle filter in a lower portion thereof, and means defining a passageway to each of the end chambers of the housing to the small particle filter.

11. The apparatus of claim 8 wherein the end walls and the adjacent partition walls are closely spaced to permit machining supports for each nozzle means and its associated receiver tube at the same time from the exterior of the end wall.

12. The apparatus of claim 8 wherein there are at least six nozzle means and associated receiver tubes mounted in the housing.

* * * * *